US008497086B2

(12) United States Patent (10) Patent No.: US 8,497,086 B2
Roche et al. (45) Date of Patent: Jul. 30, 2013

(54) **REACTION MEDIUM FOR METHICILLIN-RESISTANT *STAPHYLOCOCCUS AUREUS* (MRSA) BACTERIA**

(75) Inventors: Jean-Marc Roche, Feissons sur Salins (FR); Gilles Zambardi, Chezeneuve (FR)

(73) Assignee: Biomereux, Marcy l'Etoile (FR)

( * ) Notice: Subject to any disclaimer, the term of this patent is extended or adjusted under 35 U.S.C. 154(b) by 172 days.

(21) Appl. No.: 12/839,946

(22) Filed: Jul. 20, 2010

(65) Prior Publication Data

US 2011/0039288 A1 Feb. 17, 2011

Related U.S. Application Data

(60) Provisional application No. 61/272,072, filed on Aug. 13, 2009.

(51) Int. Cl.
*C12Q 1/14* (2006.01)
(52) U.S. Cl.
USPC .................. 435/36; 435/18; 435/19; 435/21; 435/24; 435/34
(58) Field of Classification Search
USPC .............................. 435/18, 19, 21, 24, 34, 36
See application file for complete search history.

(56) References Cited

U.S. PATENT DOCUMENTS

| | | | |
|---|---|---|---|
| 6,548,268 B1 | 4/2003 | Rambach | |
| 2003/0235879 A1 | 12/2003 | Sandberg et al. | |
| 2004/0121404 A1* | 6/2004 | Cotte et al. ..................... | 435/7.1 |
| 2004/0235012 A1* | 11/2004 | Hammann et al. ................ | 435/6 |
| 2007/0292908 A1 | 12/2007 | Robichon | |
| 2008/0145879 A1 | 6/2008 | Orenga et al. | |
| 2009/0017481 A1 | 1/2009 | Orenga et al. | |

FOREIGN PATENT DOCUMENTS

| | | |
|---|---|---|
| EP | 0 887 424 A2 | 12/1998 |
| FR | 2 790 765 A1 | 9/2000 |
| FR | 2 881 755 A1 | 8/2006 |
| JP | A 6-217760 | 8/1994 |
| JP | 07-000181 | 1/1995 |
| WO | WO 02/079486 A2 | 10/2002 |
| WO | WO 2004/027086 A1 | 4/2004 |
| WO | WO 2004/063391 A1 | 7/2004 |
| WO | WO 2007/096639 A2 | 8/2007 |
| WO | WO 2007/099254 A2 | 9/2007 |
| WO | WO 2010/040952 A2 | 4/2010 |

OTHER PUBLICATIONS

Ito, K et al. Pharmacokinetics of Cephem Antibiotics in Exudate of Pelvic Retroperitoneal Space After Radical Hysterectomy and Pelvic Lymphadenectomy. Antimicrobial Agents & Chemotherapy. 1990; vol. 34(6). pp. 1160-1164.*
Lo, Janice et al. Vancomycin and Amikacin in Cell Cultures for Virus Isolation. Pathology: The Journal of the Royal College of Pathologists of Australasia. 1996; vol. 28(4). pp. 366-369.*
Guay, DR. Cefdinir: An Advanced-Generation, Broad-spectrum Oral Cephalosporin. Clinical Therapeutics. 2002; vol. 24(4): pp. 473-89.*
Manafi et al., "Fluorogenic and Chromogenic Substrates Used in Bacterial Diagnostics," Microbiological Reviews, vol. 55, No. 3, Sep. 1991, pp. 335-348.

International Search Report issued in International Application No. PCT/FR2010/051705 dated Feb. 4, 2011 (with translation).
Written Opinion issued in International Application No. PCT/FR2010/051705 dated Feb. 4, 2011 (with translation).
Mar. 9, 2010 International Search Report issued in International Patent Application No. PCT/FR2009/051908 (with translation).
Mar. 9, 2010 Written Opinion issued in International Patent Application No. PCT/FR2009/051908 (with translation).
Jun. 1, 2010 International Search Report issued in International Patent Application No. PCT/FR2009/051909 (with translation).
Jun. 1, 2010 Written Opinion 014issued in International Patent Application No. PCT/FR2009/051909 (with translation).
Velasco et al., "Evaluation of different methods for detecting methicillin (oxacillin) resistance in *Staphylococcus aureus*," Journal of Antimicrobial Chemotherapy, Feb. 18, 2005, pp. 379-382, vol. 55, The British Society for Antimicrobial Chemotherapy 2005.
Kluytmans et al., "Performance of CHROMagar Selective Medium and Oxacillin Resistance Screening Agar Base for Identifying *Staphylococcus aureus* and Detecting Methicillin Resistance," Journal of Clinical Microbiology, Jul. 2002, pp. 2480-2482, vol. 40, No. 7, American Society for Microbiology.
Merlino et al., "Detection and expression of methicillin/oxacillin resistance in multidrug-resistant and non-multidrug-resistant *Staphylococcus aureus* in Central Sydney, Australia," Journal of Antimicrobial Chemotherapy, 2002, pp. 793-801, vol. 49, The British Society for Antimicrobial Chemotherapy.
Perry et al.; "Development and Evaluation of a Chromogenic Agar Medium for Methicillin-Resistant *Staphylococcus aureus*;" Journal of Clinical Microbiology; Oct. 2004; pp. 4519-4523; vol. 42, No. 10; American Society for Microbiology.
Athanasopoulos et al.; "Comparison of three selective chromogenic media for Methicillin-Resistant *Staphylococcus aureus* detection;" Pathologie Biologie; 2007; pp. 366-369; vol. 55; Elsevier Masson SAS (with Abstract).
Gaillot et al.; "Evaluation of CHROMagar *Staph. aureus*, a New Chromogenic Medium, for Isolation and Presumptive Identification of *Staphylococcus aureus* from Human Clinical Specimens;" Journal of Clinical Microbiology; Apr. 2000; pp. 1587-1591; vol. 38, No. 4; American Society for Microbiology.
Wertheim et al.; "Improved Detection of Methicillin Resistant *Staphylococcus aureus* Using Phenyl Mannitol Broth Containing Aztreonam and Ceftizoxime;" Journal of Clinical Microbiology; Jul. 2001; pp. 2660-2662; vol. 39, No. 7; American Society for Microbiology.
Brown et al.; "Guidelines for the laboratory diagnosis and susceptibility testing of methicillin-resistant *Staphylococcus aureus*(MRSA);" Journal of Antimicrobial Chemotherapy; 2005; pp. 1000-1018; vol. 56; Oxford University Press.
May 24, 2012 Office Action issued in U.S. Appl. No. 13/062,849.
May 14, 2012 Office Action issued in U.S. Appl. No. 13/062,768.
U.S. Appl. No. 13/062,849 in the name of Orenga et al., filed Mar. 8, 2011.
U.S. Appl. No. 13/062,768 in the name of Orenga et al., filed Mar. 8, 2011.
Dec. 3, 2012 Office Action issued in U.S. Appl. No. 13/062,849.

* cited by examiner

*Primary Examiner* — Susan Hanley
*Assistant Examiner* — Nghi Nguyen
(74) *Attorney, Agent, or Firm* — Oliff and Berridge, PLC

(57) ABSTRACT

A reaction medium for detecting and/or identifying methicillin-resistant *Staphylococcus aureus* (MRSA) bacteria includes a chromogenic substrate, a first antibiotic that belongs to the cephalosporin family and a second antibiotic that belongs to the aminoglycoside family.

16 Claims, No Drawings

REACTION MEDIUM FOR METHICILLIN-RESISTANT STAPHYLOCOCCUS AUREUS (MRSA) BACTERIA

This nonprovisional application claims the benefit of U.S. Provisional Application No. 61/272,072, filed Aug. 13, 2009.

FIELD OF THE INVENTION

The present invention relates to a reaction medium for detecting methicillin-resistant *Staphylococcus aureus* (MRSA) bacteria. The invention also relates to the use of this medium, and to a method for identifying MRSA bacteria.

BACKGROUND

Methicillin-resistant *Staphylococcus aureus* (MRSA) are *Staphylococcus aureus* strains characterized by their resistance to an antibiotic, methicillin, and to related antibiotics such as oxacillin. MRSA bacteria represent a high percentage of nosocomial infections, and are often responsible for serious and potentially fatal health problems. Most commonly cross-transmitted between patients via the healthcare staff, MRSA are responsible for endemic infections that are very difficult to control. In addition to an appropriate treatment, the screening for MRSA carriers and the isolation of colonized patients constitute the most effective methods recommended today by official organizations such as the Society for Healthcare Epidemiology of America. Early and systematic screening is therefore essential.

MRSA can be detected by various techniques.

It is possible to detect MRSA by molecular biology techniques. In this respect, mention may in particular be made of Application EP887424. However, such methods remain expensive as a routine test, and require qualified staff.

It is also possible to use conventional culture media for detecting *Staphylococcus aureus*, such as the medium described in Application EP 1390524. The detection of MRSA is carried out in an additional step, by means of a specific agglutination test (Slidex MRSA, bioMérieux) or by means of an agar diffusion method in the presence of an oxacillin, cefoxitin or latamoxef disc (recommendations of the Comité de l'Antibiogramme de la Société Française de Microbiologic (Antibiogram Committee of the French Society for Microbiology) and of the Clinical Laboratory Standard Institute).

It is also possible to culture bacteria that may be MRSA on agar media in the presence of antibiotics. Such media may also be chromogenic, thereby facilitating the reading and detection of the MRSA. Mention may in particular be made of the medium described in Application EP 1543147. However, because the detection of a phosphatase activity under the conditions described is not very specific, it is necessary to combine it with the detection of several other enzymatic activities, thereby reducing the fertility of the medium and increasing the cost thereof.

SUMMARY

Embodiments of the present invention provide a novel sensitive, specific reaction medium that enables isolation and rapid identification of methicillin-resistant *Staphylococcus aureus* (MRSA).

Surprisingly, the inventors have demonstrated that the use of combinations of antibiotics, comprising a cephalosporin and an aminoglycoside, makes it possible to obtain an excellent reaction medium for isolating and identifying methicillin-resistant *Staphylococcus aureus* (MRSA).

DETAILED DESCRIPTION OF EMBODIMENTS

The following definitions, which are in no way limiting, will make it possible to understand the invention more clearly.

For the purpose of the present disclosure, the term reaction medium is intended to mean a medium comprising all the elements necessary for survival and/or growth of microorganisms, such as *Staphylococcus aureus*.

This reaction medium may serve only as revealing medium, or as culture and revealing medium. In the first case, the microorganisms are cultured before inoculation, and in the second case, the reaction medium also constitutes the culture medium.

The reaction medium may be solid, semi-solid or liquid. The term "solid medium" is intended to mean, for example, a gelled medium. Preferably, the medium according to the invention is a gelled medium. Agar is a suitable conventional gelling agent in microbiology for culturing microorganisms, but it is also possible to use other gelling agents, for instance gelrite, gelatin or agarose. A certain number of preparations are commercial available, for instance Columbia agar, trypticase soy agar, Mac Conkey agar, Chapman agar, Sabouraud agar, or more generally those described in the Handbook of Microbiological Media (CRC Press).

Embodiments of the reaction medium may contain other optional additives such as, for example: peptones, one or more growth factors, carbohydrates, one or more selective agents, buffer solutions, one or more gelling agents, etc. The reaction medium may be in the form of a liquid or of a gel that is ready to use, e.g. ready for inoculation in a tube or a flask, or on a Petri dish. When the medium is supplied in the form of a gel in a flask, a prior regeneration (change to 100° C.) of the medium is preferably carried out before pouring into a Petri dish.

Preferably, the medium is a selective medium, i.e. a medium comprising inhibitors that favor the growth of *Staphylococcus aureus* bacteria. Mention may in particular be made of lithium chloride (LiCl), sodium azide ($NaN_3$), colistin, amphotericin, aztreonam, colimycin, sodium chloride (NaCl), deferoxamine, and/or vibriostatic compound O/129 (2,4-diamino-6,7-diisopropylpteridine).

The substrate for an enzymatic or metabolic activity is chosen from any substrate that can be hydrolyzed to give a product that allows the direct or indirect detection of an enzymatic activity or of a metabolism, such as, in particular, an osidase activity, preferably a glucuronidase, glucosidase or galactosidase activity.

The substrate may be a natural or synthetic substrate. The metabolism of the substrate causes a variation in the physicochemical properties of the reaction medium or of the cells of organisms. This variation can preferably be detected by physicochemical methods, preferably optical methods visible to the unaided eye of the (human) operator, or by means of spectrometric, electrical, magnetic, etc., instruments. Preferably, the variation is a variation in optical properties, such as a modification of absorption, of fluorescence or of luminescence.

In the present disclosure, the term "coloration" is used to cover a coloration, which is absorption of light in the visible spectrum, or a fluorescence, which is absorption at one wavelength ($\lambda$ex) and emission at a different wavelength ($\lambda$em, e.g., $\lambda$em>$\lambda$ex).

For the purpose of the present disclosure, the term chromogenic substrate is intended to mean any substrate that can be hydrolyzed to give a product that allows direct or indirect detection of an enzymatic activity, such as an osidase activity, preferably an alpha-glucosidase activity, an esterase activity, preferably a phosphatase activity, or a peptidase activity, preferably a coagulase activity.

Mention may in particular be made of substrates based on indoxyl, flavone, alizarin, acridine, phenoxazine, nitrophenol, nitroaniline, naphthol, catechol, hydroxyquinoline, coumarin or hydroxyphenylquinoxazol-4-one. Preferred substrates are indoxyl-based.

As alpha-glucosidase substrate, mention may more particularly be made of the substrates 5-bromo-6-chloro-3-indoxyl-alpha-glucoside; dihydroxyflavone-alpha-glucoside; 3,4-cyclohexenoesculetin-alpha-glucoside; 8-hydroxyquinoline-alpha-glucoside; 5-bromo-4-chloro-3-indoxyl-alpha-glucoside; 5-bromo-4-chloro-3-indoxyl-N-methyl-alpha-glucoside; 6-chloro-3-indoxyl-alpha-glucoside; 5-bromo-3-indoxyl-alpha-glucoside; 5-iodo-3-indoxyl-alpha-glucoside; 6-fluoro-3-indoxyl-alpha-glucoside; alizarin-alpha-glucoside; nitrophenyl-alpha-glucoside; 4-methylumbelliferyl-alpha-glucoside; naphtholbenzein-alpha-glucoside; indoxyl-N-methyl-alpha-glucoside; naphthyl-alpha-glucoside; aminophenyl-alpha-glucoside; dichloroaminophenyl-alpha-glucoside. Preferred alpha-glucosidase substrates are 5-bromo-4-chloro-3-indoxyl-N-methyl-alpha-glucoside or 5-bromo-4-chloro-3-indoxyl-alpha-glucoside.

As phosphatase substrate, mention may more particularly be made of the substrates 5-bromo-6-chloro-3-indoxyl phosphate; 3,4-cyclohexenoesculetin phosphate; 5-bromo-4-chloro-3-indoxyl phosphate; 5-bromo-4-chloro-3-indoxyl-N-methyl phosphate; 6-chloro-3-indoxyl phosphate; 5-bromo-3-indoxyl phosphate; 5-iodo-3-indoxyl phosphate; 6-fluoro-3-indoxyl phosphate; nitrophenyl phosphate; 4-methylumbelliferyl phosphate; indoxyl-N-methyl phosphate; naphthyl phosphate, ELF97-phosphate (2-5'-chloro-2'-phosphoryloxyphenyl)-6-chloro-4-(3H)-quinazolinone). A preferred phosphatase substrate is 6-chloro-3-indoxyl phosphate.

The substrate used in the present invention may be in combination with other substrates, such as a substrate for an osidase, esterase (e.g., phosphatase or phospholipase) or peptidase (e.g., coagulase). For example, the medium may comprise two alpha-glucosidase substrates.

Substrates can be used in a wide pH range, for example between pH 5.5 and 10, preferably between 6.5 and 9.

For the purpose of the present disclosure, an antibiotic that belongs to the cephalosporin family is preferably an antibiotic chosen from:

A first-generation cephalosporin, such as: cefalexin, cefaloridine, cefalotin, cefazolin, cefadroxil, cefazedone, cefatrizine, cefapirine, cefradine, cefacetrile, cefrodaxine, ceftezole.

A second-generation cephalosporin, such as: cefoxitin, cefuroxime, cefamandole, cefaclor, cefotetan, cefonicide, cefotiam, loracarbef, cefmetazole, cefprozil, ceforanide, cefminox.

A third-generation cephalosporin, such as: cefotaxime, ceftazidime, cefsulodine, ceftriaxone, cefinenoxime, latamoxef, ceftizoxime, cefixime, cefodizime, cefetamet, cefpiramide, cefoperazone, cefpodoxime, ceftibuten, cefdinir, cefditoren, ceftriaxone, cefoperazone, cefbuperazone, cefdinir, A fourth-generation cephalosporin, such as cefepime, cefpirome.

Use of future-generation cephalosporins is also contemplated. The antibiotic that belongs to the cephalosporin family is preferably cefminox or cefdinir.

For the purpose of the present disclosure, an antibiotic that belongs to the aminoglycoside family is preferably an antibiotic chosen from amikacin, gentamicin, isepamicin, kanamycin, netilmicin, streptomycin and tobramycin.

The antibiotic that belongs to the aminoglycoside family is preferably amikacin or kanamycin.

The term biological sample is intended to mean a clinical sample, for example derived from a bronchial, tracheal or pulmonary aspiration specimen, a pleural fluid specimen, a bronchoalveolar lavage specimen, an expectoration specimen, a blood specimen or a lung biopsy specimen, or a joint fluid or pericardial fluid specimen; a biological fluid or a food sample, derived from any type of food; or a surface specimen. The sample may be liquid or solid, and mention may be made, in a nonlimiting manner, of a clinical sample of blood, plasma, urine or feces, or of specimens from the nose, perineum, throat, skin, wounds or cerebrospinal fluid, or a food sample.

The term "sample" is therefore intended to mean the specimen in itself (swab, stools, foods, etc.) and also colonies of microorganisms derived from said specimen (for example after isolation on a gelled culture medium, or in an enrichment broth inoculated with said specimen).

Embodiments relate to a reaction medium for detecting and/or identifying methicillin-resistant *Staphylococcus aureus* (MRSA) bacteria, comprising a chromogenic substrate, a first antibiotic that belongs to the cephalosporin family and a second antibiotic that belongs to the aminoglycoside family.

According to some embodiments of the invention, said first antibiotic is cefminox or cefdinir. Preferably, the cefminox concentration is between 10 and 35 mg/l, preferably between 12 and 28 mg/l. Preferably, the cefdinir concentration is between 0.1 and 1 mg/l, preferably between 0.2 and 0.6 mg/l.

According to some embodiments of the invention, said second antibiotic is kanamycin or amikacin. Preferably, the kanamycin concentration is between 0.2 and 1.5 mg/l, preferably between 0.5 and 1.25 mg/l. Preferably, the amikacin concentration is between 0.5 and 5 mg/l, preferably between 1 and 2 mg/l.

According to some embodiments, the combination of two antibiotics comprises cefminox and kanamycin.

According to other embodiments, the combination of two antibiotics comprises cefminox and amikacin.

According to other embodiments, the combination of two antibiotics comprises cefdinir and kanamycin.

According to other preferred embodiments, the combination of two antibiotics comprises cefdinir and amikacin.

According to embodiments, said chromogenic substrate allows the detection of an osidase, esterase or peptidase activity.

According to embodiments, said osidase activity is an alpha-glucosidase activity.

The substrate for an alpha-glucosidase activity is preferably an indoxyl-alpha-glucoside. Preferably, the substrate is 5-bromo-4-chloro-3-indoxyl-alpha-glucoside (X-alpha-glucoside) or 5-bromo-4-chloro-3-indoxyl-N-methyl-alpha-glucoside (Green A-alpha-glucoside). Preferably, the substrate is present in the medium at a concentration of between 0.01 and 0.2 g/l, preferably between 0.03 and 0.15 g/l. At this substrate concentration, a better coloration contrast may be obtained.

According to embodiments, the esterase activity is a phosphatase activity. Preferably, the substrate used is 6-chloro-3- indoxyl phosphate (pink-phosphate). Preferably, this substrate is present in the medium at a concentration of between 0.05 and 0.5 g/l, preferably between 0.1 and 0.4 g/l. At this substrate concentration, a better coloration contrast may be obtained.

According to embodiments, the reaction medium also comprises a second enzyme substrate. Preferably, said second substrate is an alpha-glucosidase substrate. Preferably, said first substrate is an alpha-glucosidase substrate, preferably an X-alpha-glucoside (5-bromo-4-chloro-3-indoxyl-alpha-glucoside) and said second substrate is an alpha-glucosidase substrate, preferably Green A-alpha-glucoside (5-bromo-4-chloro-3-indoxyl-N-methyl-alpha-glucoside).

According to embodiments, the medium also comprises at least one inhibitor that favors the growth of *Staphylococcus aureus* bacteria, such as lithium chloride (LiCl), sodium azide (NaN$_3$), colistin, amphotericin, aztreonam, polymyxins, sodium chloride (NaCl) and/or deferoxamine.

According to embodiments, the medium also comprises a mixture of inhibitors, for example comprising four inhibitors that favor the growth of *Staphylococcus aureus* bacteria, said inhibitors preferably being LiCl, vibriostatic compound O/129, aztreonam and/or amphotericin.

Embodiments also relate to in vitro use of a reaction medium as defined above, for isolating and identifying methicillin-resistant *Staphylococcus aureus* (MRSA) bacteria.

Embodiments also relate to a method for detecting and/or identifying methicillin-resistant *Staphylococcus aureus* (MRSA) bacteria in a biological sample, comprising:
 a) inoculating the biological sample that may contain methicillin-resistant *Staphylococcus aureus* (MRSA) bacteria on a reaction medium as defined above;
 b) incubating;
 c) identifying the colonies as being MRSA colonies.

The incubation is preferably carried out at a temperature of between 30° C. and 42° C. The MRSA are preferably detected by one or two α-glucosidase activities or a phosphatase activity that makes it possible to obtained colored or fluorescent colonies. Other species of *Staphylococcus* appear colorless or have a color or fluorescence different from that of the *S. aureus* colonies.

Step a) may, for example, be preceded by a step of pre-enrichment in a selective or nonselective medium.

Embodiments also relate to a reaction medium for detecting and/or identifying methicillin-resistant *Staphylococcus aureus* (MRSA) bacteria, comprising a substrate for an enzymatic or metabolic activity, a first antibiotic chosen from cefdinir and cefminox, and a second antibiotic that belongs to the aminoglycoside family.

Preferably, the cefminox concentration is between 10 and 35 mg/l, preferably between 12 and 28 mg/l. Preferably, the cefdinir concentration is between 0.1 and 1 mg/l, preferably between 0.2 and 0.6 mg/l.

According to embodiments, the second antibiotic is kanamycin or amikacin. Preferably, the kanamycin concentration is between 0.2 and 1.5 mg/l, preferably between 0.5 and 1.25 mg/l. Preferably, the amikacin concentration is between 0.5 and 5 mg/l, preferably between 1 and 2 mg/l.

According to embodiments, the combination of two antibiotics comprises cefminox and kanamycin.

According to embodiments, the combination of two antibiotics comprises cefminox and amikacin.

According to embodiments, the combination of two antibiotics comprises cefdinir and kanamycin.

According to embodiments, the combination of two antibiotics comprises cefdinir and amikacin.

According to embodiments, the substrate for an enzymatic or metabolic activity allows detection of an osidase, esterase or peptidase activity.

According to embodiments, the osidase activity is an alpha-glucosidase activity.

The substrate for an alpha-glucosidase activity is preferably an indoxyl-alpha-glucoside. Preferably, the substrate is 5-bromo-4-chloro-3-indoxyl-alpha-glucoside (X-alpha-glucoside) or 5-bromo-4-chloro-3-indoxyl-N-methyl-alpha-glucoside (Green A-alpha-glucoside). Preferably, this substrate is present in the medium at a concentration of between 0.01 and 0.2 g/l, preferably between 0.03 and 0.15 g/l. At this substrate concentration, better coloration contrast may be obtained.

According to embodiments, the esterase activity is a phosphatase activity. Preferably, the substrate used is 6-chloro-3-indoxyl phosphate (pink-phosphate). Preferably, this substrate is present in the medium at a concentration of between 0.05 and 0.5 g/l, preferably between 0.1 and 0.4 g/l. At this substrate concentration, better coloration contrast may be obtained.

According to embodiments, the reaction medium also comprises a second enzyme substrate. Preferably, said second substrate is an alpha-glucosidase substrate. Preferably, said first substrate is an alpha-glucosidase substrate, preferably X-alpha-glucoside (5-bromo-4-chloro-3-indoxyl-alpha-glucoside) and said second substrate is an alpha-glucosidase substrate, preferably Green A-alpha-glucoside (5-bromo-4-chloro-3-indoxyl-N-methyl-alpha-glucoside).

According to embodiments, the medium also comprises at least one inhibitor that favors the growth of *Staphylococcus aureus* bacteria, such as lithium chloride (LiCl), sodium azide (NaN$_3$), colistin, amphotericin, aztreonam, polymyxins, sodium chloride (NaCl) and/or deferoxamine.

According to embodiments, the medium also comprises a mixture of inhibitors, for example comprising four inhibitors that favor the growth of *Staphylococcus aureus* bacteria, said inhibitors preferably being LiCl, vibriostatic compound O/129, aztreonam and amphotericin.

Embodiments also relate to in vitro use of a reaction medium as defined above, for isolating and identifying methicillin-resistant *Staphylococcus aureus* (MRSA) bacteria.

Embodiments also relate to a method for detecting and/or identifying methicillin-resistant *Staphylococcus aureus* (MRSA) bacteria in a biological sample, comprising:
 a) inoculating the biological sample that may contain methicillin-resistant *Staphylococcus aureus* (MRSA) bacteria on a reaction medium as defined above;
 b) incubating;
 c) identifying the colonies as being MRSA colonies.

The incubation is preferably carried out at a temperature of between 30° C. and 42° C.

The MRSA are preferably detected by one or two alpha-glucosidase activities or a phosphatase activity that makes it possible to obtain colored or fluorescent colonies. Other species of *Staphylococcus* appear colorless or have a color or fluorescence different from that of the *S. aureus* colonies.

Step a) may be preceded by a step of pre-enrichment in a selective or nonselective medium.

The following examples are given by way of illustration and are in no way limiting in nature. They will make it possible to understand the invention more clearly.

EXAMPLE 1

MRSA Medium Comprising a Cefminox-Kanamycin Antibiotic Combination and Various Chromogenic Substrates 1. Preparation of the Media The media tested in the experiments were the following:

Medium T: chromID™ MRSA control medium (bioMérieux, ref. 43 451).

Medium A: medium T, the cefoxitin being substituted with a cefminox (Daewoo Chemical, A8060902; 16 mg/l)/kanamycin (Sigma, ref. K4000; 1 mg/l) antibiotic combination, the chromogenic substrate being pink-phosphate (Biosynth, ref. C-5100; 0.25 g/l).

Medium B: medium T, the cefoxitin being substituted with a cefminox (16 mg/l)/kanamycin (0.75 mg/l) antibiotic combination, the chromogenic substrate being X-alpha-glucoside (Biosynth, B7230; 0.045 g/l) and Green A-alpha-glucoside (Inalco, ref. 1758-0730).

Medium C: medium T, the cefoxitin being substituted with a cefminox (16 mg/l)/kanamycin (0.75 mg/l) antibiotic combination, the chromogenic substrates being X-alpha-glucoside (Biosynth, B7230; 0.045 g/l) and Green A-alpha-glucoside (Inalco, ref. 1758-0730, 0.08 g/l).

2. Inoculation and Reading of Media

Various methicillin-resistant (MRSA) or methicillin-sensitive (MSSA) strains of *S. aureus* bacteria, and coagulase-negative staphylococcal strains (CoNS), all derived from a bioMérieux collection, were suspended in physiological saline, and then inoculated on the medium, according to the four-quadrant streaking technique. The dishes were incubated at 37° C. for 24 hours. The colonies formed were examined visually after 18 h and 24 hours of incubation.

3. Results:

The results obtained are shown in Table 1.

| Medium | MRSA detected/ MRSA tested | MSSA + CoNS detected/ MSSA + CoNS tested |
| --- | --- | --- |
| T | 18/20 | 1/15 |
| A | 20/20 | 5/18 |
| B | 19/20 | 4/15 |
| C | 29/35 | 4/24 |

These results show an excellent sensitivity of the media according to the invention. In particular, medium A made it possible to detect all MRSA.

EXAMPLE 2

MRSA Medium Comprising Cefminox and Kanamycin at Various Concentrations

1. Preparation of the Media

The media tested in the experiments were the following:

Medium T: chromID™ MRSA control medium as in Example 1.

Medium D: medium T, the cefoxitin being substituted with a cefminox (antibiotic identical to that used in Example 1)/kanamycin (antibiotic identical to that used in Example 1) combination of antibiotics, at various concentrations, the chromogenic substrates being X-alpha-glucoside (substrate identical to that used in Example 1; 0.045 g/l) and Green A-alpha-glucoside (substrate identical to that used in Example 1; 0.08 g/l).

|  | cefminox in mg/l | kanamycin in mg/l |
| --- | --- | --- |
| D1 | 16 | 0.75 |
| D2 | 16 | 1 |
| D3 | 14 | 0.75 |
| D4 | 14 | 1 |

2. Inoculation and Reading of Media

This step was carried out as in Example 1.

3. Results:

The results obtained are shown in Table 2 below.

| Medium | MRSA detected/ MRSA tested | MSSA + CoNS detected/ MSSA + CoNS tested |
| --- | --- | --- |
| T | 18/20 | 1/15 |
| D1 | 19/20 | 1/18 |
| D2 | 15/18 | 0/18 |
| D3 | 16/18 | 1/18 |
| D4 | 16/18 | 1/18 |

These results show that a cefminox concentration of 16 mg/l and a kanamycin concentration of 0.75 mg/l provide excellent specificity and sensitivity.

EXAMPLE 3

MRSA Medium Comprising a Cefminox-Amikacin Antibiotic Combination and Various Chromogenic Substrates 1. Preparation of the Media The media tested in the experiments were the following:

Medium T: chromID™ MRSA control medium as in Example 1.

Medium E: medium T, the cefoxitin being substituted with a cefminox (antibiotic identical to that used in Example 1; 16 mg/l)/amikacin (Sigma, ref. 2324; 2 mg/l) antibiotic combination, the chromogenic substrate being pink-phosphate (Biosynth, C-5100; 0.25 g/l).

Medium F: medium T, the cefoxitin being substituted with a cefminox (16 mg/l)/amikacin (2.5 mg/l) antibiotic combination, the chromogenic substrates being X-alpha-glucoside (substrate identical to that used in Example 1; 0.045 g/l) and Green A-alpha-glucoside (substrate identical to that used in Example 1; 0.08 g/l).

2. Inoculation and Reading of Media

This step was carried out as in Example 3

3. Results:

The results obtained are shown in Table 3 below.

| Medium | MRSA detected/ MRSA tested | MSSA + CoNS detected/ MSSA + CoNS tested |
| --- | --- | --- |
| T | 18/20 | 1/15 |
| E | 20/20 | 3/15 |
| F | 19/20 | 6/24 |

These results show that antibiotic combinations according to the invention provide excellent sensitivity, irrespective of the substrate used.

EXAMPLE 4

MRSA Medium Comprising Cefdinir and Amikacin

1. Preparation of the Media

The media tested in the experiments were the following:

Medium T: chromID™ MRSA control medium as in Example 1.

Medium G: medium T, the cefoxitin being substituted with a cefdinir (CDR 0806007)/amikacin (antibiotic identical to that used in Example 3) combination of antibiotics at various concentrations, the chromogenic substrate being pink-phosphate (substrate identical to that used in Example 3; 0.25 g/l).

|    | cefdinir in mg/l | amikacin in mg/l |
|----|------------------|------------------|
| G1 | 0.3              | 2                |
| G2 | 0.2              | 2                |

Medium H: medium T, the cefoxitin being substituted with a cefdinir/amikacin combination of antibiotics, at various concentrations, the chromogenic substrate being X-alpha-glucoside (substrate identical to that used in Example 1; 0.045 WI) and Green A-alpha-Glu (substrate identical to that used in Example 1, 0.08 g/l).

|    | cefdinir in mg/l | amikacin in mg/l |
|----|------------------|------------------|
| H1 | 0.3              | 2                |
| H2 | 0.2              | 2                |

2. Inoculation and Reading of Media

This step was carried out as in Example 1.

3. Results:

The results obtained are shown in Table 4 below.

| Medium | MRSA detected/ MRSA tested | MSSA + CoNS detected/ MSSA + CoNS tested |
|--------|----------------------------|------------------------------------------|
| T      | 18/20                      | 1/15                                     |
| G1     | 20/20                      | 0/15                                     |
| G2     | 20/20                      | 1/15                                     |
| H1     | 18/20                      | 1/15                                     |
| H2     | 19/20                      | 2/15                                     |

These results show that cefdinir/amikacin antibiotic combinations according to the invention provide excellent sensitivity and specificity, irrespective of the concentration used.

EXAMPLE 5

Analyses of Clinical Specimens on MRSA Media

1. Preparation of the Media

The media tested in the experiments were the following:

Medium T: chromID™ MRSA control medium as in Example 1.

Batch 1: 0.08 g/l Green A-alpha-Glu+0.045 g/l X-alpha-Glu, 16 mg/l cefminox+0.75 mg/l kanamycin.

Batch 2: 0.08 g/l Green A-alpha-Glu+0.045 g/l X-alpha-Glu, 0.3 mg/l cefdinir+2 mg/l amikacin.

Batch 3: 0.25 g/l pink-phosphate, 16 mg/l cefminox+2 mg/l amikacin.

Batch 4: 0.25 g/l pink-phosphate, 0.3 mg/l cefdinir+2 mg/l amikacin.

The substrates and antibiotics used were the same as those used in the previous examples.

2. Inoculation and Reading of Media

Two studies were carried out in parallel using various clinical specimens (nose, throat, perineum, wound), which were suspended in physiological saline, and inoculated so as to give isolated colonies on the medium, according to the four-quadrant streaking technique. The dishes were incubated at 37° C. for 24 hours. The colonies formed were examined visually after 18 h and 24 hours of incubation.

3. Results:

The results obtained are shown in the tables below.

First study:

| Parameters  | Time | Medium T | Batch 1 | Batch 2 | Batch 3 | Batch 4 |
|-------------|------|----------|---------|---------|---------|---------|
| Detection   | 18 h | 15/19    | 17/19   | 16/19   | 18/19   | 18/19   |
| sensitivity | 24 h | 18/19    | 19/19   | 19/19   | 19/19   | 19/19   |
| Specificity | 24 h | 97%      | 86%     | 88%     | 82%     | 80%     |

Second study:

| Parameters  | Time | Medium T | Batch 1 | Batch 2 | Batch 3 | Batch 4 |
|-------------|------|----------|---------|---------|---------|---------|
| Detection   | 18 h | 48/60    | 49/60   | 31/60   | 47/60   | 54/60   |
| sensitivity | 24 h | 56/60    | 54/60   | 42/60   | 48/60   | 57/60   |
| Specificity | 24 h | 95%      | 93%     | 89%     | 99%     | 98%     |

These results show that antibiotic combinations according to the invention exhibited excellent detection sensitivity from 18 h onwards.

What is claimed is:

1. A reaction medium for detecting and/or identifying methicillin-resistant *Staphylococcus aureus* (MRSA) bacteria, comprising a chromogenic substrate, a first antibiotic that belongs to the cephalosporin family and a second antibiotic that belongs to the aminoglycoside family, wherein the second antibiotic is at a concentration from 0.75 to 2.5 mg/l.

2. The reaction medium according to claim 1, wherein said first antibiotic is cefminox or cefdinir.

3. The reaction medium according to claim 1, wherein said second antibiotic is kanamycin or amikacin.

4. The reaction medium according to claim 1, wherein said chromogenic substrate allows the detection of a glycosidase, esterase or peptidase activity.

5. The reaction medium according to claim 1, wherein said chromogenic substrate allows for the detection of an alpha-glucosidase activity.

6. The reaction medium according to claim 1, wherein said chromogenic substrate allows for the detection of a phosphatase activity.

7. The reaction medium according to claim 1, further comprising LiCl, vibriostatic compound O/129, aztreonam and amphotericin.

8. A method for detecting and/or identifying methicillin-resistant *Staphylococcus aureus* (MRSA) bacteria in a biological sample, comprising:
   a) inoculating the biological sample on the reaction medium according to claim 1;
   b) incubating the inoculated medium of step a);

c) determining whether there is a variation of a physicochemical property in the incubated medium of step b); and d) identifying colonies as MRSA colonies, when MRSA bacteria is present in the biological sample, in areas where a variation of a physicochemical property has been detected.

9. The method according to claim 8, wherein the physicochemical property is an optical property visible to an unaided human eye.

10. The reaction medium according to claim 1, wherein the second antibiotic is kanamycin at a concentration from 0.75 to 1.5 mg/l.

11. The reaction medium according to claim 1, wherein the second antibiotic is amikacin at a concentration from 1 to 2.5 mg/l.

12. The reaction medium according to claim 1, wherein the first antibiotic is cefminox at a concentration from 10 to 35 mg/l or cefdinir at a concentration from 0.1 to 1 mg/l.

13. The reaction medium according to claim 1, further comprising aztreonam and vibriostatic compound O/129.

14. A reaction medium for detecting and/or identifying methicillin-resistant *Staphylococcus aureus* (MRSA) bacteria, comprising a chromogenic substrate, a first antibiotic that belongs to the cephalosporin family and a second antibiotic that belongs to the aminoglycoside family, wherein:

the second antibiotic is at a concentration from 0.2 to 1.5 mg/l when the second antibiotic is kanamycin; and the second antibiotic is at a concentration from 0.5 to 5 mg/l when the second antibiotic is amikacin.

15. The reaction medium according to claim 14, wherein the second antibiotic is kanamycin.

16. The reaction medium according to claim 14, wherein the second antibiotic is amikacin.

* * * * *

UNITED STATES PATENT AND TRADEMARK OFFICE
CERTIFICATE OF CORRECTION

| | | |
|---|---|---|
| PATENT NO. | : 8,497,086 B2 | Page 1 of 1 |
| APPLICATION NO. | : 12/839946 | |
| DATED | : July 30, 2013 | |
| INVENTOR(S) | : Jean-Marc Roche et al. | |

It is certified that error appears in the above-identified patent and that said Letters Patent is hereby corrected as shown below:

Title Page, Item (73) Assignee:

Delete "Biomereux" and insert --bioMerieux--, therefor.

Signed and Sealed this
Eleventh Day of March, 2014

Michelle K. Lee
*Deputy Director of the United States Patent and Trademark Office*